(12) United States Patent
Ockenfuss

(10) Patent No.: US 10,670,455 B2
(45) Date of Patent: Jun. 2, 2020

(54) SPECTROSCOPIC ASSEMBLY AND METHOD

(71) Applicant: Viavi Solutions Inc., Milpitas, CA (US)

(72) Inventor: Georg J. Ockenfuss, Santa Rosa, CA (US)

(73) Assignee: VIAVI Solutions Inc., San Jose, CA (US)

(*) Notice: Subject to any disclaimer, the term of this patent is extended or adjusted under 35 U.S.C. 154(b) by 192 days.

(21) Appl. No.: 15/427,906

(22) Filed: Feb. 8, 2017

(65) Prior Publication Data

US 2017/0191870 A1   Jul. 6, 2017

Related U.S. Application Data

(63) Continuation of application No. 14/012,855, filed on Aug. 28, 2013, now Pat. No. 9,568,362, which is a (Continued)

(51) Int. Cl.
*G02B 5/08* (2006.01)
*G02B 5/20* (2006.01)
(Continued)

(52) U.S. Cl.
CPC .......... *G01J 1/0488* (2013.01); *A61B 5/0059* (2013.01); *A61B 5/0071* (2013.01);
(Continued)

(58) Field of Classification Search
CPC .......... G01J 3/00; G01J 3/0229; G01J 3/0208; G01J 3/021; G01J 3/0237; G01J 3/0256;
(Continued)

(56) References Cited

U.S. PATENT DOCUMENTS 4,029,394 A   6/1977   Araki
4,979,803 A   12/1990  McGuckin et al.
(Continued)

FOREIGN PATENT DOCUMENTS

CN   1669332 A   9/2005
CN   1227521 C   11/2005
(Continued)

OTHER PUBLICATIONS

Whitehurst et al., "Fluorescence-based Implantable Glucose Sensor with Smartphone Interface" presented at the 48th European Association for the Study of Diabetes (EASD) Annual Meeting in Berlin, Germany, T.K., 2012.
(Continued)

*Primary Examiner* — William R Alexander
*Assistant Examiner* — Balram T Parbadia
(74) *Attorney, Agent, or Firm* — Harrity & Harrity, LLP

(57) ABSTRACT

A spectrometer assembly is provided having an optical transmission filter including a stack of continuous, non-patterned alternating dielectric and metal layers. Angle-dependent transmission wavelength shift of the optical transmission filter with continuous metal layers is small e.g. in comparison with multilayer dielectric filters, facilitating size reduction of the spectrometer assembly.

22 Claims, 12 Drawing Sheets

Related U.S. Application Data continuation-in-part of application No. 13/720,728, filed on Dec. 19, 2012, now Pat. No. 9,448,346.

(51) Int. Cl.

| | | |
|---|---|---|
| *G01J 1/04* | (2006.01) | |
| *G01J 3/02* | (2006.01) | |
| *G01N 21/64* | (2006.01) | |
| *G02B 5/28* | (2006.01) | |
| *G01J 3/44* | (2006.01) | |
| *A61B 5/00* | (2006.01) | |
| *A61B 5/145* | (2006.01) | |
| *A61B 5/1455* | (2006.01) | |
| *A61B 5/1459* | (2006.01) | |
| *G01J 1/42* | (2006.01) | |
| *G01J 3/12* | (2006.01) | |

(52) U.S. Cl.
CPC .......... *A61B 5/0075* (2013.01); *A61B 5/1455* (2013.01); *A61B 5/1459* (2013.01); *A61B 5/14532* (2013.01); *G01J 1/42* (2013.01); *G01J 3/0229* (2013.01); *G01J 3/0256* (2013.01); *G01J 3/4406* (2013.01); *G01N 21/645* (2013.01); *G02B 5/285* (2013.01); *A61B 2562/0233* (2013.01); *A61B 2562/12* (2013.01); *G01J 2003/1226* (2013.01)

(58) Field of Classification Search
CPC .... G01J 3/26; G01J 3/36; G01J 3/4406; G01J 3/0437; G01J 3/02; G01J 3/0205; G01J 3/0235; G02B 5/005; G02B 5/08; G02B 5/09; G02B 5/20; G02B 5/28; G02B 5/286; G02B 5/26; G02B 5/208; G02B 5/281; G02B 5/282; G02B 5/283; G02B 21/16; G02B 21/06; G02B 21/361; G02B 21/365; G02B 2207/113; F21V 9/04; F21V 9/06
See application file for complete search history.

(56) References Cited

U.S. PATENT DOCUMENTS

| | | |
|---|---|---|
| 4,979,807 A | 12/1990 | McGuckin et al. |
| 5,120,622 A | 6/1992 | Hanrahan |
| 5,337,191 A | 8/1994 | Austin |
| 5,422,730 A | 6/1995 | Barlow et al. |
| 5,528,082 A | 6/1996 | Ho |
| 5,577,020 A * | 11/1996 | Utsunomiya ..... G11B 11/10586 360/112 |
| 5,587,090 A | 12/1996 | Belcher et al. |
| 5,648,653 A | 7/1997 | Sakamoto et al. |
| 5,711,889 A | 1/1998 | Buchsbaum |
| 5,784,507 A | 7/1998 | Holm-Kennedy et al. |
| 5,808,293 A | 9/1998 | Yang |
| 6,031,653 A | 2/2000 | Wang |
| 6,034,820 A | 3/2000 | Someno et al. |
| 6,057,925 A | 5/2000 | Anthon |
| 6,238,583 B1 | 5/2001 | Edlinger et al. |
| 6,278,540 B1 | 8/2001 | Wang |
| 6,383,894 B1 | 5/2002 | Wester |
| 6,565,770 B1 | 5/2003 | Mayer et al. |
| 6,638,668 B2 | 10/2003 | Buchsbaum et al. |
| 6,783,900 B2 | 8/2004 | Venkataraman |
| 6,809,859 B2 | 10/2004 | Erdogan et al. |
| 7,045,471 B2 | 5/2006 | Kobayashi |
| 7,078,779 B2 | 7/2006 | Wang |
| 7,079,252 B1 | 7/2006 | Debreczeny et al. |
| 7,119,960 B1 | 10/2006 | Erdogan et al. |
| 7,133,197 B2 | 11/2006 | Ockenfuss et al. |
| 7,230,779 B2 | 6/2007 | Kunii |
| 7,648,808 B2 | 1/2010 | Buchsbaum et al. |
| 7,708,945 B1 | 5/2010 | Abel et al. |
| 7,875,947 B2 | 6/2011 | Moon et al. |
| 8,274,051 B1 | 9/2012 | Aswell |
| 8,300,313 B2 | 10/2012 | Pradhan et al. |
| 8,587,080 B2 | 11/2013 | Gidon et al. |
| 8,958,156 B1 | 2/2015 | Erdogan et al. |
| 9,317,162 B2 | 4/2016 | Kuo |
| 9,448,346 B2 | 9/2016 | Ockenfuss |
| 9,568,362 B2 | 2/2017 | Ockenfuss |
| 2002/0074513 A1 | 6/2002 | Abel et al. |
| 2002/0163641 A1 | 11/2002 | Shroder |
| 2003/0038941 A1 | 2/2003 | Potyrailo et al. |
| 2003/0103150 A1 | 6/2003 | Catrysse et al. |
| 2004/0135921 A1 | 7/2004 | Murata et al. |
| 2004/0218187 A1 | 11/2004 | Cole et al. |
| 2005/0068534 A1 | 3/2005 | Kleinfeld et al. |
| 2005/0110999 A1 | 5/2005 | Erdogan et al. |
| 2006/0180886 A1 | 8/2006 | Tsang |
| 2007/0097691 A1 | 5/2007 | Wu |
| 2007/0139772 A1 * | 6/2007 | Wang ................... G02B 5/3083 359/487.03 |
| 2008/0055717 A1 | 3/2008 | Pradhan et al. |
| 2008/0316628 A1 | 12/2008 | Nakajima et al. |
| 2009/0109537 A1 | 4/2009 | Bright et al. |
| 2009/0194668 A1 | 8/2009 | Kong |
| 2009/0273745 A1 | 11/2009 | Lin |
| 2009/0302407 A1 | 12/2009 | Gidon et al. |
| 2009/0315131 A1 | 12/2009 | Hung et al. |
| 2010/0067000 A1 | 3/2010 | Baumberg |
| 2010/0072568 A1 | 3/2010 | Park |
| 2010/0105035 A1 | 4/2010 | Hashsham et al. |
| 2010/0149483 A1 | 6/2010 | Chiavetta, III et al. |
| 2010/0201926 A1 | 8/2010 | Lee |
| 2010/0202734 A1 | 8/2010 | DeCorby |
| 2011/0204463 A1 | 8/2011 | Grand |
| 2012/0044491 A1 | 2/2012 | Urushidani |
| 2012/0085944 A1 | 4/2012 | Gidon et al. |
| 2012/0092666 A1 | 4/2012 | Meijer |
| 2012/0156714 A1 | 6/2012 | O'Brien et al. |
| 2012/0187512 A1 | 7/2012 | Wang et al. |
| 2013/0020503 A1 | 1/2013 | Geddes |
| 2013/0043551 A1 | 2/2013 | Yoshizawa |
| 2013/0188254 A1 * | 7/2013 | Li ........................... G02B 5/284 359/589 |
| 2013/0307107 A1 | 11/2013 | Tsai et al. |
| 2014/0014838 A1 | 1/2014 | Hendrix et al. |
| 2014/0168761 A1 | 6/2014 | Ockenfuss |
| 2017/0068025 A1 | 3/2017 | Ockenfuss et al. |
| 2017/0191871 A1 | 7/2017 | Ockenfuss et al. |

FOREIGN PATENT DOCUMENTS

| | | |
|---|---|---|
| CN | 101604700 B | 12/2012 |
| DE | 4442045 | 5/1996 |
| JP | S591542407 | 8/1984 |
| JP | H08107107 A | 4/1996 |
| JP | 2001255666 A | 9/2001 |
| JP | 2002023063 A | 1/2002 |
| JP | 2006190958 A | 7/2006 |
| JP | 2006227432 A | 8/2006 |
| JP | 2007219515 A | 8/2007 |
| JP | 2008008975 A | 1/2008 |
| JP | 2008276112 A | 11/2008 |
| JP | 2009102717 A | 5/2009 |
| JP | 2009545150 A | 12/2009 |
| JP | 2010128259 A | 6/2010 |
| JP | 2011243862 A | 12/2011 |
| JP | 2013015827 A | 1/2013 |
| JP | 2013041027 A | 2/2013 |
| TW | M427564 | 4/2012 |
| TW | 201250548 A | 12/2012 |
| WO | WO2007037553 A1 | 5/2007 |

OTHER PUBLICATIONS

Mu et al., "Design and Fabrication of a High Transmissivity Metal-Dielectric Ultraviolet Band-Pass Filter", Appl. Phys. Lett. 102, 2013.

(56) References Cited

OTHER PUBLICATIONS

Weidemaier et al., "Multi-Day Pre-Clinical demonstration of Glucose/Galactose Binding Protein-Based Fiber Optic Sensor", Biosensors and Bioelectronics, BIOS-4442, Elsevier B.V., 2011.

Ebbesen et al., "Extraordinary Optical Transmission Through Sub-Wavelength Hole Arrays", Letters to Nature, vol. 391, pp. 667-669, Feb. 12, 1998.

Tao et al., "A Wavelength Demultiplexing Structure Based on Metal-Dielectric-Metal Plasmonic Nano-Capillary Resonators", Optics Express 11111, vol. 18, No. 11, May 24, 2010.

Search Report for corresponding European application No. 13196813.3, of US patent application, dated Mar. 28, 2014.

Search Report for corresponding European application No. 13196812.5 dated Mar. 17, 2014.

Dandin et al., "Optical filtering technologies for integrated fluorescence sensors", Lab on a Chip, vo. 7, No. 8, p. 955, Jan. 1, 2007.

Webster et al., "Monolithic Capillary Electrophoresis Device With Integrated Fluorescence Detector", Analytical chemistry, American Chemical Society, US, vol. 73, No. 7, pp. 1622-1626, Apr. 1, 2001.

Dobowolski et al., "Metal/Dielectric Transmission Interference Filters With Low Reflectance. 1. Design" Applied Optics, vol. 34, No. 25, pp. 5673-5683, Sep. 1, 1995.

Sullivan et al., "Metal/Dielectric Transmission Interference Filters With Low Reflectance. 2. Experimental Results" Applied Optics, vol. 34, No. 25, pp. 5684-5685, Sep. 1, 1995.

Holm-Kennedy, Koon Wing Tsang, Wah Wai Sze, Fenglai Jiang, "A Novel monolithic, chip-integrated, color spectrometer: The distributed wavelength filter component", 1991, University of Hawaii, SPIE vol. 1527 Current Developments in Optical Design and Optical Engineering, pp. 322-331.

Dandin et al., "Optical filtering technologies for integrated fluorescence sensors", The Royal Society of Chemistry, 2007, pp. 955-977.

Holm-Kennedy et al., "A Novel monolithic, chip-integrated, color spectrometer: The distributed wavelength filter component", Current Developments in Optical Design and Optical Engineering, SPIE vol. 1527, 1991, pp. 323-331.

Partial European Search Report corresponding to EP 14 89 5400, dated Jan. 17, 2018, 12 pages.

Extended European Search Report corresponding to EP 14 89 5400, dated Apr. 18, 2016, 10 pages.

International Search Report from corresponding PCT application No. PCT/US2014/043041.

Extended European Search report for Application No. EP13196812.5, dated Jul. 25, 2014, 13 pages.

Sullivan B.T., et al., "Metal/Dielectric Transmission Interference Filters with Low Reflectance. 2. Experimental Results," Applied Optics, vol. 34(25), Sep. 1, 1995, pp. 5684-5694, XP000522996.

Written Opinion for Application No. PCT/US2014/043041, dated Jan. 2, 2015, 8 pages.

\* cited by examiner

SPECTROSCOPIC ASSEMBLY AND METHOD

CROSS-REFERENCE TO RELATED APPLICATIONS

This application is a continuation of U.S. patent application Ser. No. 14/012,855, filed Aug. 28, 2013 (now U.S. Pat. No. 9,568,362), which is a continuation in part of U.S. patent application Ser. No. 13/720,728, filed Dec. 19, 2012 (now U.S. Pat. No. 9,448,346), which are incorporated herein by reference.

TECHNICAL FIELD

The present invention relates to spectroscopic instrumentation and methods, and in particular to spectroscopic instrumentation and methods employing optical filters.

BACKGROUND OF THE INVENTION

Transmission optical filters are used in spectroscopic applications to select a wavelength or a band of wavelengths of light emitted by a sample, and/or to select a wavelength or a band of wavelengths of light illuminating the sample. For example, in a fluorescence spectroscopic application, a beam of excitation light illuminates a sample, and light at a longer wavelength is detected to obtain its optical spectrum and/or to determine a total level of fluorescence emitted by the sample in response to excitation by the excitation light.

A single bandpass transmission optical filter can be used to measure the total level of fluorescence. The fluorescence levels measurement can be used to determine a concentration of fluorophore molecules, pH level, and the like. The fluorescence measurement can also be used to evaluate a concentration of non-fluorescent target molecules in a sample, by providing fluorophore molecules designed to change their fluorescence properties upon binding to the target molecules. The sample containing the fluorophore and target molecules is illuminated with the excitation light, and the optical power level of the fluorescent light is measured.

A typical spectrofluorometer suitable for the above purpose is shown in FIG. 1. The spectrofluorometer 10 includes a light source 11, collimating/focusing lenses 12A, 12B, and 12C, an excitation filter 13, a fluorescence filter 14, a beamsplitter 15, and a photodetector 16. In operation, the light source 11 emits excitation light 17 shown with solid lines. The excitation light 17 is collimated by the leftmost lens 12A, filtered by the excitation filter 13, transmitted through the beamsplitter 15, and is focused by a rightmost lens 12B onto a sample 18. The illuminated sample 18 emits fluorescent light 19 shown with dashed lines. The fluorescent light 19 is collimated by the rightmost lens 12B, reflects from the beamsplitter 15, and is focused by the bottom lens 12C onto the photodetector 16. The excitation and fluorescence filters 13 and 14 are multilayer dielectric filters, which are preferred over other types of filters for their good wavelength selectivity and a comparatively low optical insertion loss.

The spectrofluorometer 10, although widely used, has a drawback of a relatively large size. Nowadays, miniature fluorometers can be used in implantable glucose measurement probes deployed subcutaneously, that is, under skin of human patients. For example, Senseonics Inc. of Germantown, Calif., USA, developed a continuous blood glucose monitoring system intended for diabetes patients. The monitoring system includes a subcutaneous probe having a miniature fluorometer as a blood glucose sensor.

Due to subcutaneous placement of the spectrofluorometer, the latter needs to be made as small as possible. It is a goal of the invention to provide filters which enable a compact spectrometer assembly suitable for under-skin placement. Other numerous applications of miniature spectrometer assemblies using these filters are of course possible.

SUMMARY OF THE INVENTION

One factor that impedes miniaturization of spectrometers is necessity to collimate optical beams to ensure sufficient wavelength selectivity of optical filters used in the spectrometers. To collimate optical beams, lenses or concave mirrors are required. These elements are relatively bulky, and require free-space propagation for at least one focal length, which increases the size of the spectrometer assembly.

In accordance with the invention, a spectrometer assembly includes an optical filter that can preserve a suitable wavelength selectivity even in a highly converging or diverging optical beam, thereby alleviating the need for collimating optical elements and reducing size. A filter for such a spectrometer assembly includes a stack of continuous, non-micro-structured alternating dielectric and metal layers, which results in lessening of angular sensitivity of the transmission wavelength.

Optical filters containing metal layers are known, and they have been generally avoided in spectrometers due to a relatively high insertion loss in the metal layers. To reduce the insertion loss, the metal layers could be micro-structured to include a plurality of sub-wavelength conductive features exhibiting a plasmon resonance effect negating the loss. However, micro-structured metal layers exhibit a considerable angular sensitivity of the transmission wavelength, and thus are not used in the invention. Instead, the invention uses continuous and non-micro-structured metal layers sandwiched between dielectric layers. The thicknesses and positions of the continuous, non-micro-structured metal layers in the resulting layer stack are selected so as to induce a relatively high optical transmission, while preserving wavelength selectivity of the optical filter at a wide range of angles of incidence.

In accordance with the invention, there is provided a spectrometer assembly comprising:

a holder for holding a sample for emitting signal light when excited with excitation light;

a first signal filter coupled to the holder, for transmitting a first portion of the signal light at a first signal transmission wavelength, while blocking the excitation light; and a first photodetector coupled to the first signal filter, for providing a first electrical signal upon illumination with the first portion of the signal light transmitted through the first signal filter, wherein the first signal filter includes continuous, non-micro-structured metal and dielectric layers stacked in alternation, whereby angular sensitivity of the first signal transmission wavelength is lessened.

Similar optical filters can be provided in the spectrometer assembly for the excitation optical path, to transmit the excitation light while blocking the signal light. More than one filter can be provided for either the excitation or the detection paths. The excitation filter or filters can be coupled to the light source; and each detection filter can be coupled to its own photodetector. The filters can be manufactured integrally with the photodetector and/or the light source.

In some embodiments, the total thickness of the metal and dielectric layers in the filter(s) is less than 5 micrometers. Preferably, each of the metal layers has a tapered edge at a periphery of the filter, wherein each tapered edge is protectively covered by one or more of the dielectric layers. Such filters are particularly useful in aggressive or corrosive environments, due to their inherent corrosion resistance.

In accordance with the invention, there is further provided a method of detecting fluorescence, comprising
 (a) providing the spectrometer assembly above;
 (b) illuminating the sample with the excitation light;
 (c) collecting the first portion of the signal light in a collection angle of at least 60 degrees; and
 (d) detecting the electrical signal of the photodetector.

In accordance with another aspect of the invention, there is further provided a use of a transmission optical filter in an optical spectrometer, the transmission optical filter including continuous, non-micro-structured metal and dielectric layers stacked in alternation, to discriminate between excitation and signal wavelengths, wherein the presence of the continuous, non-patterned metal layers in the optical filter lessens angular dependence of a transmission wavelength of the optical filter, thereby lessening a size of the optical spectrometer.

BRIEF DESCRIPTION OF THE DRAWINGS

Exemplary embodiments will now be described in conjunction with the drawings, in which.

DETAILED DESCRIPTION OF THE INVENTION

While the present teachings are described in conjunction with various embodiments and examples, it is not intended that the present teachings be limited to such embodiments. On the contrary, the present teachings encompass various alternatives and equivalents, as will be appreciated by those of skill in the art.

Figure 1:
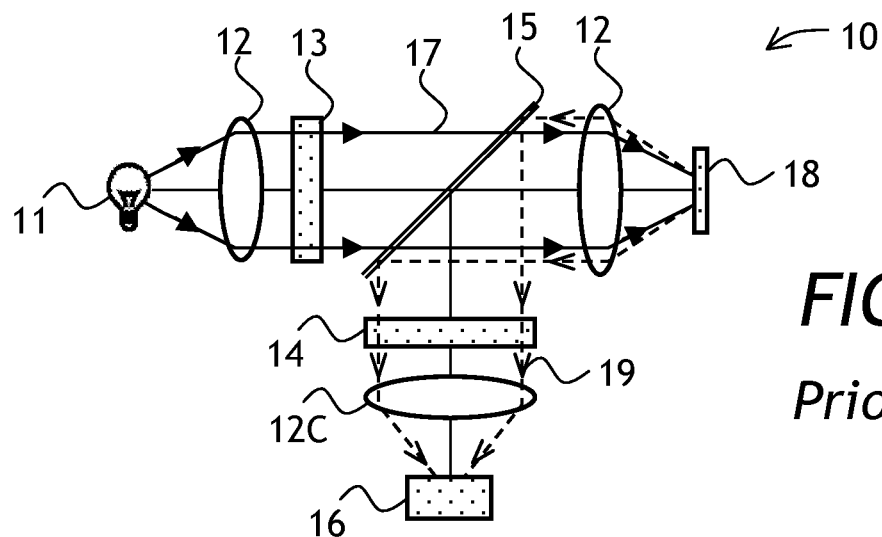
FIG. 1 is a plan view of a prior-art spectrofluorometer.
Figure 2A:
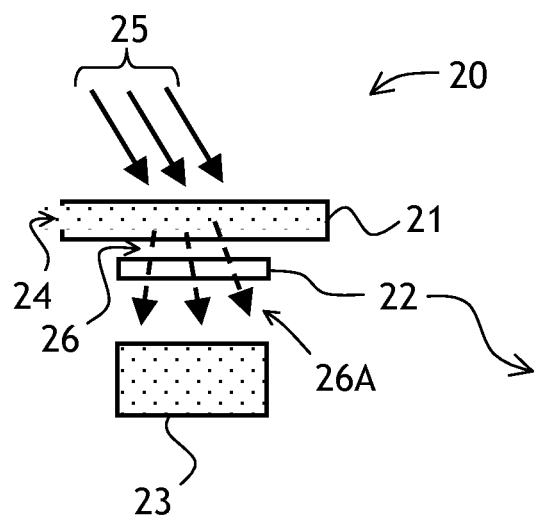
FIG. 2A is a side cross-sectional exploded view of a spectrometer assembly of the invention.
Figure 2B:
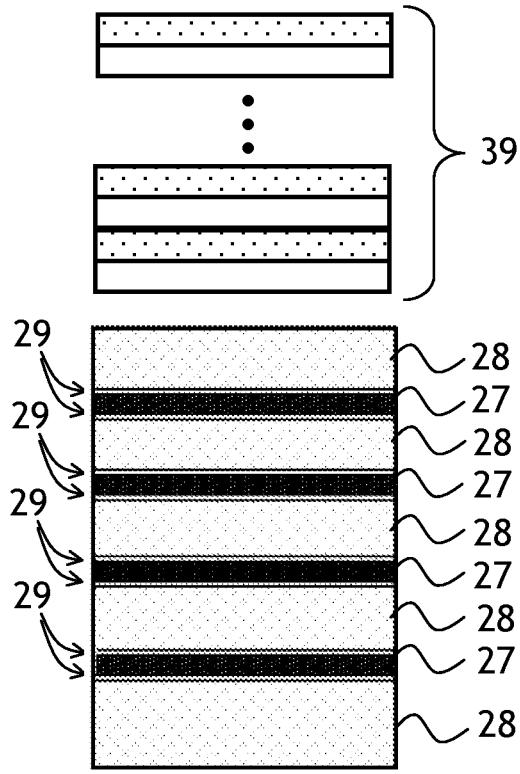
FIG. 2B is a side cross-sectional view of an optical filter used in the spectrometer assembly of FIG. 2A.
Figure 3:
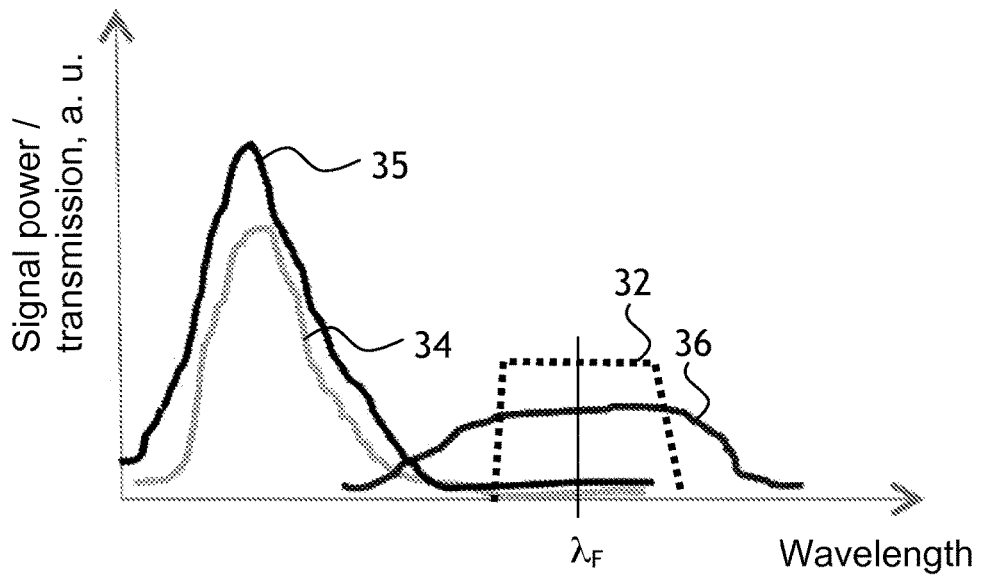
FIG. 3 is a plot of absorption and fluorescence spectra of a sample, superimposed with an emission spectrum of a light source and a transmission spectrum of the filter of FIG. 2B.

Referring to FIG. 2A and FIG. 3, a spectrometer assembly 20 of FIG. 2A includes a sample holder 21, an optical filter 22 (or "signal filter 22") optically coupled to the sample holder 21, and a photodetector 23 optically coupled to the signal filter 22. The sample holder 21 holds a sample 24, for example a fluid having a fluorescent dye or protein dissolved therein. The sample holder 21, the signal filter 22, and the photodetector 23 can be held together by a housing, not shown, or simply attached together into a stack. In operation, the sample 24 is excited with excitation light 25 having a spectrum 35 of FIG. 3, preferably matching an absorption or excitation spectrum 34 of the sample 24. The excitation light 25 is emitted by an external source, not shown in FIG. 2A. In response, the sample 24 emits signal light 26, in this example fluorescence light having an emission spectrum 36. The signal filter 22 transmits a portion 26A of the signal light 26 at a transmission wavelength $\lambda_F$ (FIG. 3), while blocking the excitation light 25 (FIG. 2) and, preferably, stray light. The transmitted portion 26A impinges onto the photodetector 23 generating an electrical signal, not shown, proportional to the optical power level of the transmitted portion 26A. Herein and throughout the rest of the specification, the term "light at a wavelength $\lambda$" denotes light in a wavelength band of a finite width, centered around $\lambda$. In other words, the wavelength $\lambda$ is a center wavelength of a wavelength band of a finite width. By way of example, in FIG. 3, the wavelength $\lambda_F$ is a center wavelength of a transmission band 32 of the signal filter 22.

Turning to FIG. 2B with further reference to FIG. 2A and FIG. 3, the signal filter 22 includes continuous, non-micro-structured metal 27 and dielectric 28 layers stacked in alternation, as shown. Optional barrier layers 29 facilitate sealing of the metal layers 27. A metal with good optical qualities, such as silver, aluminum or gold, is preferably used to deposit the metal layers 27. The dielectric layers 28 can include a metal oxide, such as $SiO_2$, $Ta_2O_5$, $Nb_2O_5$, $TiO_2$, $HfO_2$, and $Al_2O_3$, or mixtures of these oxides. The metal layers 27 thickness can be selected individually, to better match required optical properties, such as the magnitude of optical transmission, the central wavelength $\lambda_F$, and the transmission band 32 (FIG. 3).

The metal layers 27 are typically 5 nm to 50 nm thick, and preferably 8 nm to 30 nm thick. The dielectric layers 28 are 10 nm to 500 nm thick, and preferably 20 nm to 200 nm thick. There are typically two to eight metal layers 27 in a single filter, and more preferably three to six metal layers 27. The resulting filter 22 thickness is usually less than 5 micrometers, and more preferably less than 1 micrometer. The barrier layers 29 are very thin, often less than three, preferably less than one nanometer in thickness, layers of a metal oxide, for example zinc oxide. To obtain a barrier layer, a metal can be deposited to the required thickness of 0.5 nm, with the subsequent oxidation of the metal. Commercially available software, such as Optilayer™ provided by OptiLayer Ltd., Moscow, Russian Federation, TFCalc™ provided by Software Spectra Inc., Portland, Oreg., USA, or FilmStar™ provided by FTG Software, Princeton, N.J. USA, can be used to optimize the metal and dielectric layer thicknesses.

To increase the attenuation in selected wavelength ranges an additional stack 39 of dielectric layers can be added to the signal filter 22; e.g. in case of the signal filter the optional stack 39 could be a quarter-wave stack centered at the excitation wavelength. Furthermore, the metal 27 and dielectric 28 layers of the signal filter 22 can be deposited directly onto the photodetector 23, making the filter 22 integral with the photodetector 23. It can be convenient, for example, to deposit the signal filter 22 directly onto a CMOS or ASIC wafer having integrated photodetectors therein.

It is important that the metal layers 27 be continuous, non-micro-structured layers having no structure etched, or otherwise formed therein. Structured metal-dielectric filters can show a high magnitude of transmission, but that is usually achieved at a cost of high angular sensitivity of the transmission wavelength(s). This latter phenomenon has been reported, for example, by Ebbesen et al. in *Letters to Nature*, Vol. 391, p. 667-669 (1998). In contradistinction, the signal filter 22 of the invention, is absent any such structures, which enables the signal filter 22 to be much less sensitive to the incidence angle of the signal light 26 than a micro-structured metal-dielectric filter of Ebbesen. Herein, the term "micro-structured" refers to wavelength-size or sub-wavelength-size features shaped and sized to exhibit a plasmon resonance effect, for example 10 nm to 2 nm in size for visible and near infrared light. The "features" can include rectangles, grids, ellipsoids, and similar structures. Filters of the present invention can be structured for other purposes, for example environmental and mechanical stability, with feature size of larger than 2 um, and more preferably larger than 200 um. Accordingly, the term "non-micro-structured" refers to either completely smooth and continuous films, or to films that are structured, but are absent a pattern of features therein smaller than 2 um in size, and more preferably absent a pattern of features smaller than 200 um in size. Features that large usually do not exhibit an appreciable plasmon resonance effect in the UV to NIR (Near Infrared) spectral range, and thus are not considered "micro-structures" in this disclosure.

When the filter's 22 transmission wavelength $\lambda_F$ does not change appreciably with the angle of incidence, a collimating lens may be omitted in the spectrometer assembly 20 as shown, enabling the spectrometer assembly 20 to be very compact, and/or improving light collection efficiency. The angular dependence of the transmission wavelength $\lambda_F$ of the signal filter 22 in comparison with traditional multilayer dielectric filters, and a more detailed exemplary method of manufacture of an embodiment of the signal filter 22, will be considered further below.

Figure 4A:
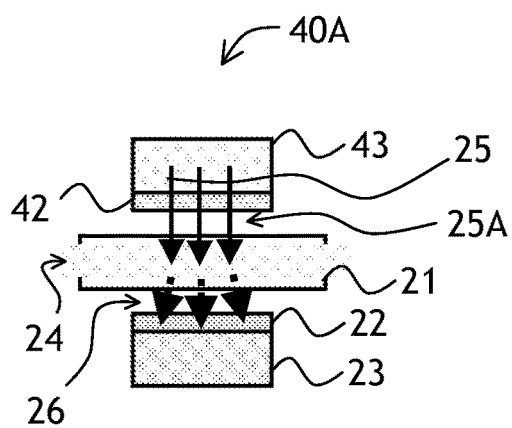
FIGS. 4A to 4D are side cross-sectional views of different embodiments of spectrometer assemblies of the invention.
Figure 6A:
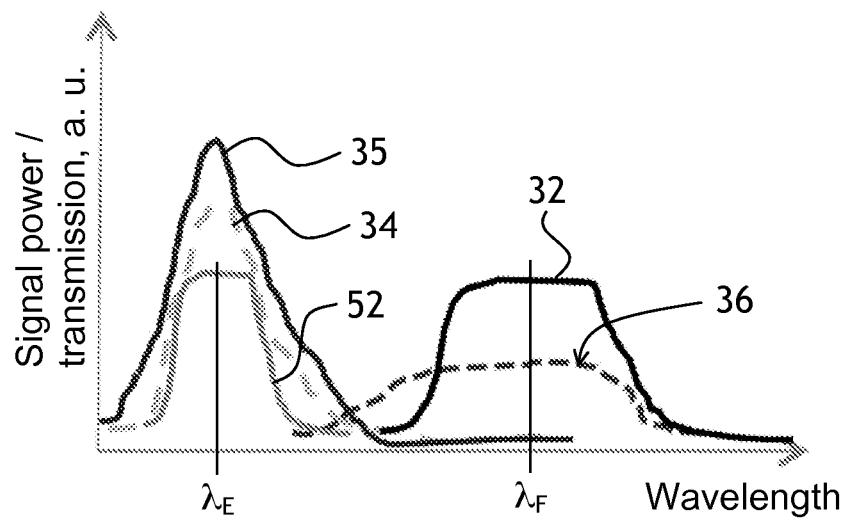
FIGS. 6A to 6C are spectral plots of absorption/fluorescence of a sample usable with the spectrometer assembly of FIG. 5, superimposed with an emission spectrum of a light source and a transmission spectrum of the filter of FIG. 2B.

Turning now to FIGS. 4A and 6A with further reference to FIGS. 2A and 2B, a spectrometer assembly 40A includes the sample holder 21, the signal filter 22 coupled to the sample holder 21, and the photodetector 23 coupled to the signal filter 22. The sample holder 21 holds the sample 24. The spectrometer assembly 40A further includes an excitation light source 43 and an excitation filter 42 coupled to the excitation light source 42 and to the sample holder 21. The excitation filter 42 is preferably of a same type as the signal filter 22 of FIG. 2B, that is, it includes continuous, non-micro-structured metal 27 and dielectric 28 layers stacked in alternation, for lessening angular dependence of its transmission wavelength ("emission wavelength") $\lambda_E$ (FIG. 6A). In operation, the light source 42 (FIG. 4A) emits the excitation light 25 having the spectrum 35 (FIG. 6A), and the excitation filter 42 (FIG. 4A) transmits a portion 25A of the excitation light 25 at the emission wavelength $\lambda_E$ (FIG. 6A), while blocking the signal light 26. The emission wavelength $\lambda_E$ is a center wavelength of a transmission band 52 of the excitation optical filter 42. The spectrometer assembly 40A can be used in applications where the sample holder 21 can be made in form of a tube or channel accessible on both sides, for example in a flow cytometer application.

Figure 4B:
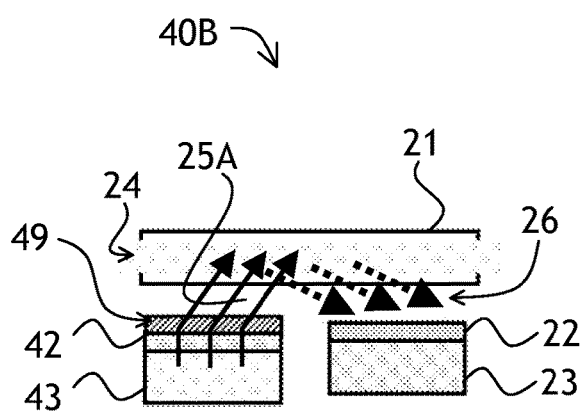
Figure 4C:
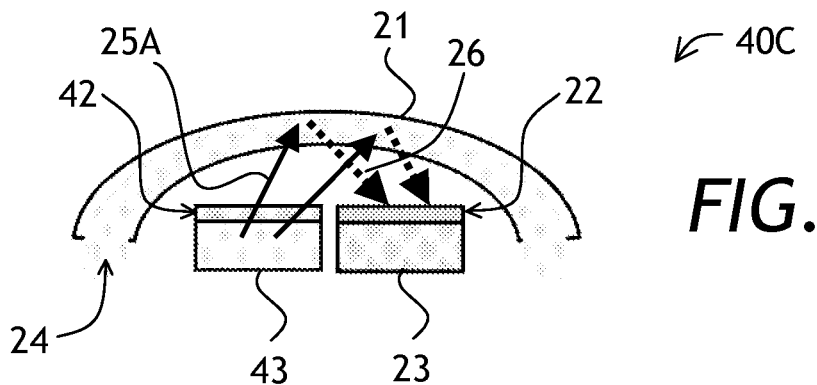
Figure 4D:
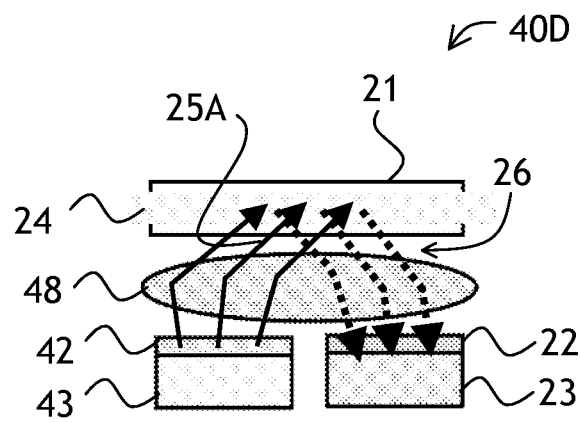

Referring to FIGS. 4B to 4D with further reference to FIG. 4A, the spectrometer assemblies 40B, 40C, and 40D of FIGS. 4B, 4C, and 4D, respectively, are similar to the spectrometer assembly 40A of FIG. 4A. One difference is that in the spectrometer assemblies 40B to 40D of FIGS. 4B to 4D, the excitation 42 and signal 22 optical filters are disposed on a same side of the sample holder 21. In FIG. 4B, an optional light-shaping diffuser 49 is coupled to the excitation filter 42, for directing the excitation light portion 25A onto the sample 24 at an angle, towards the transmission filter 22 and the photodetector 23. In FIG. 4C, the sample holder 21 is curved around the excitation 42 and signal 22 optical filters, to improve light exposure. In FIG. 4D, an optional single lens 48 is used both for directing the excitation light portion 25A onto the sample 24, and for collecting the signal light 26 on the signal filter 22.

Advantageously, the metal 27 and dielectric 28 layers of the excitation 42 and signal 22 optical filters of the spectrometer assemblies 40A to 40D of FIGS. 4A to 4D, respectively, can be deposited directly onto the light source 43 and/or the photodetector 23, respectively, making the optical filters 42 and 22 integral with the respective light source 43 and the photodetector 23.

The placement of the excitation 42 and signal 22 optical filters, and the light source 43 and the photodetector 23 on a same side of the sample holder 21 makes the spectrometer assemblies 40B, 40C, and 40D of FIGS. 4B, 4C, and 4D particularly suitable for sensor applications, because the opposite side of the sample holder 21, that is, the top side in FIGS. 4B to 4D, can be conveniently exposed to an environment being sensed. By way of a non-limiting example, the sample 24 can include marker fluorophore molecules, which change their fluorescence properties upon binding to target molecules, thereby indicating the presence of the target molecules in the sample 24. Concentration of such target molecules can be evaluated by measuring the strength, or the optical power, of the fluorescence signal 26. For example, one can use fluorophores that bind to glucose molecules, to measure blood glucose concentration. A miniature glucose concentration meter using the spectrometer assembly 40B of FIG. 4B will be described further below.

Figure 5:
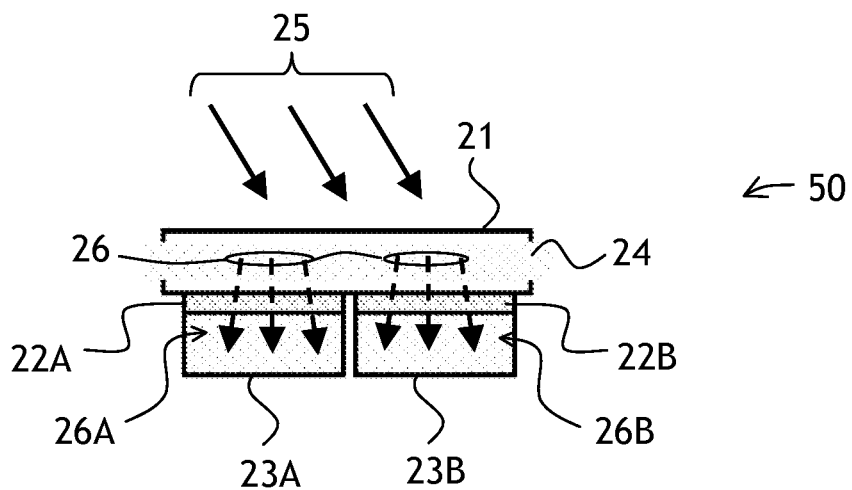
FIG. 5 is a side cross-sectional view of a spectrometer assembly having two fluorescence filters and two photodetectors.
Figure 6B:
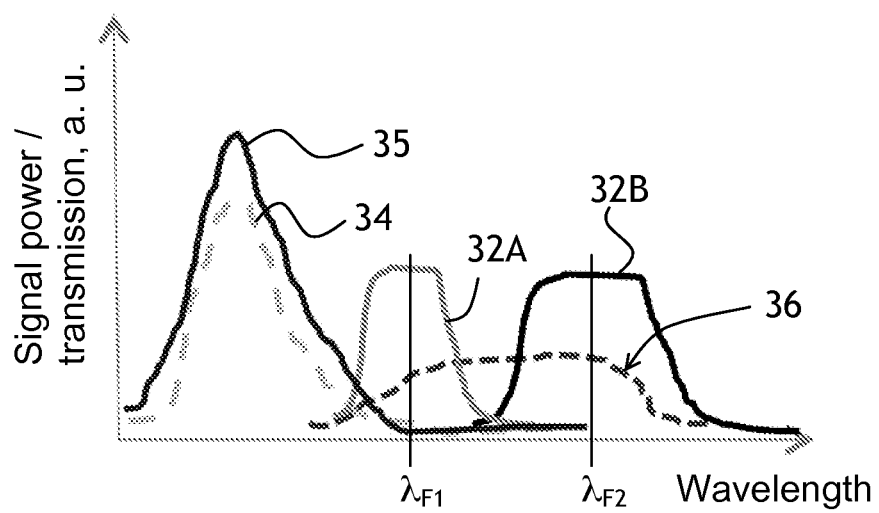

Turning to FIGS. 5 and 6B with further reference to FIGS. 2A and 2B, a spectrometer assembly 50 of FIG. 5 is similar to the spectrometer assembly 20 of FIG. 2A. One difference is that the spectrometer assembly 50 of FIG. 5 includes not one but two signal filters 22A and 22B coupled to the sample holder 21. In operation, the two signal filters 22A and 22B transmit first 26A and second 26B portions of the signal light 26 at central wavelengths $\lambda_{F1}$ and $\lambda_{F2}$ of corresponding wavelength bands 32A and 32B (FIG. 6B), while blocking the excitation light 25 having the emission spectrum 35. In FIG. 5, first 23A and second 23B photodetectors are coupled to the first 22A and second 22B signal filters, respectively. When illuminated with the first 26A and second 26B portions of the signal light 26, the first 23A and second 23B photodetectors generate respective first and second electrical signals, not shown, proportional to the respective optical power levels of the first 26A and second 26B portions of the signal light 26. At least one, and preferably both, the first and second signal filters 22A and 22B include the continuous, non-micro-structured metal 27 and dielectric 28 layers stacked in alternation, as illustrated in FIG. 2B, for lessening angular dependence of the central wavelengths $\lambda_{F1}$ and $\lambda_{F2}$, respectively.

Figure 6C:
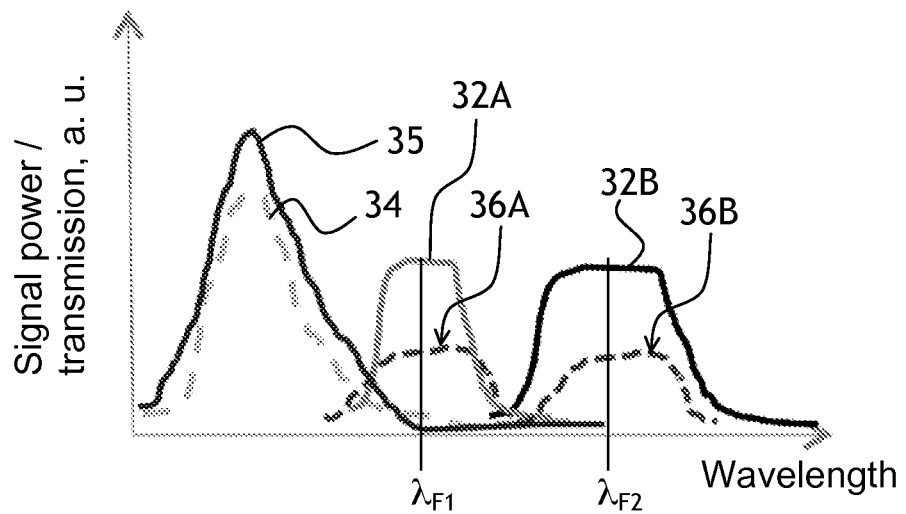

The spectrometer assembly 50 can be used in an application where the marker fluorophores change spectral distribution of the fluorescence 36 upon binding to target molecules. The ratio of the first and second electrical signals can serve as an indicator of binding the marker fluorophore to the target molecules, as disclosed by Weidemaier et al. in an article entitled "Multi-day pre-clinical demonstration of glucose/galactose binding protein-based beroptic sensor", *Biosens. Bioelectron.* (2011). Alternatively, two different marker fluorophores can be used to indicate concentration of two different target molecules, or some other parameters the fluorescence light 36 is sensitive to. Referring to FIG. 6C, fluorescence spectra 36A and 36B correspond to two different marker fluorophores, not shown. The fluorescence spectrum 36A of the first fluorophore is aligned with the transmission band 32A of the first filter 22A, and the fluorescence spectrum 36B of the second fluorophore is aligned with the transmission band 32B of the second filter 22B. The concentrations of the two different target molecules can be evaluated independently.

In one embodiment of the invention, the transmission band 32B of the second optical filter 22B is aligned not with the fluorescence spectrum 36 but with the emission spectrum 35, transmitting scattered excitation light 25 at a the excitation wavelength $\lambda_E$, while blocking the signal light 26. This allows one to evaluate the strength of the excitation light 25 by measuring scattering of the excitation light 25 in the sample 24. Knowing the strength of the excitation light 25 allows one to reference, or normalize, the fluorescence strength measurement.

Figure 7:
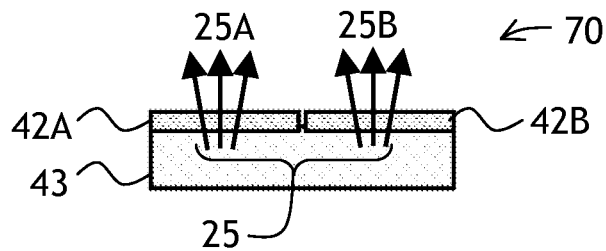
FIG. 7 is a cross-sectional view of a subassembly including a light source and two excitation filters, usable with the spectrometer assemblies of FIG. 2A, FIGS. 4A to 4D, and FIG. 5.
Figure 8A:
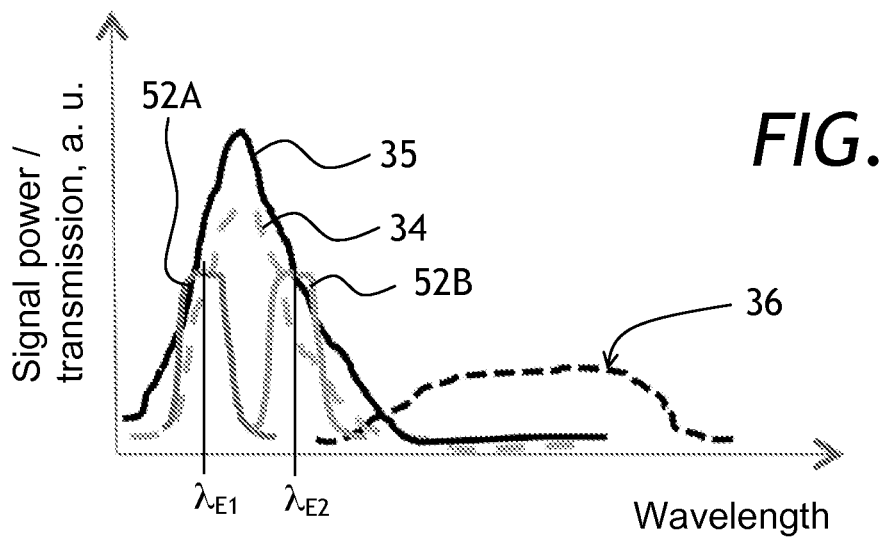
FIGS. 8A and 8B are emission spectral plots of the light source of FIG. 7 superimposed with absorption/fluorescence spectra of a sample and the transmission spectra of the excitation filters of FIG. 7.
Figure 8B:
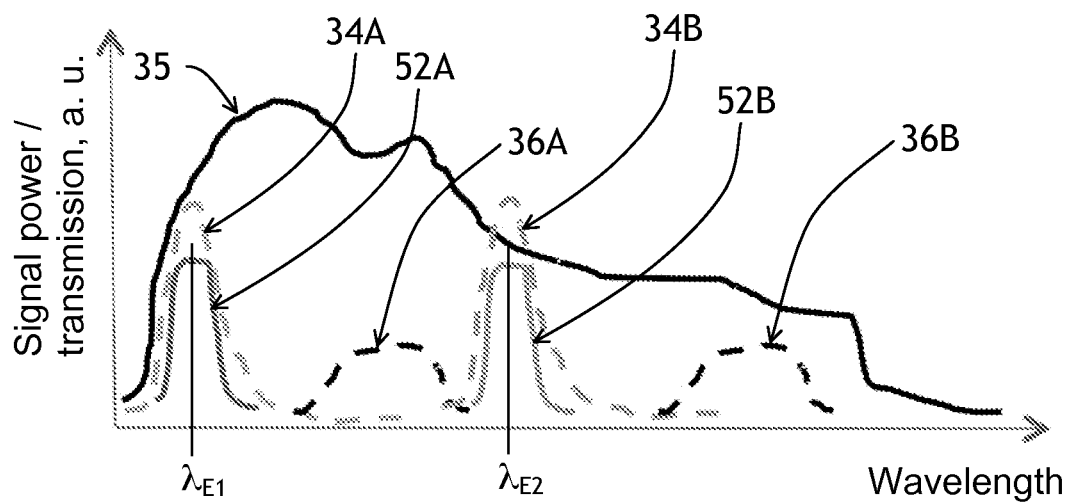

In some applications of the invention, multiple excitation wavelength bands may be required. Turning to FIG. 7, FIG. 8A, and FIG. 8B, with further reference to FIG. 2B, a subassembly 70 includes the light source 43, and first 42A and second 42B emission filters coupled to the common light source 43 having the emission spectrum 35 (FIGS. 8A and 8B). In operation, the first and second emission filters 42A and 42B (FIG. 7) transmit first 25A and second 25B portions of the excitation light 25 in wavelength bands 52A and 52B having central wavelengths $\lambda_{E1}$ and $\lambda_{E2}$, respectively (FIGS. 8A and 8B), while blocking the signal light 26 In FIG. 8B, the two distinct excitation wavelength bands 52A and 52B match absorption bands 34A and 34B of two distinct fluorophores, not shown, causing the fluorophores to emit fluorescence in two distinct fluorescence bands 36A and 36B. At least one, and preferably both, the first and second emission filters 22A and 22B include the continuous, non-micro-structured metal 27 and dielectric 28 layers stacked in alternation, as illustrated in FIG. 2B.

Figure 9A:
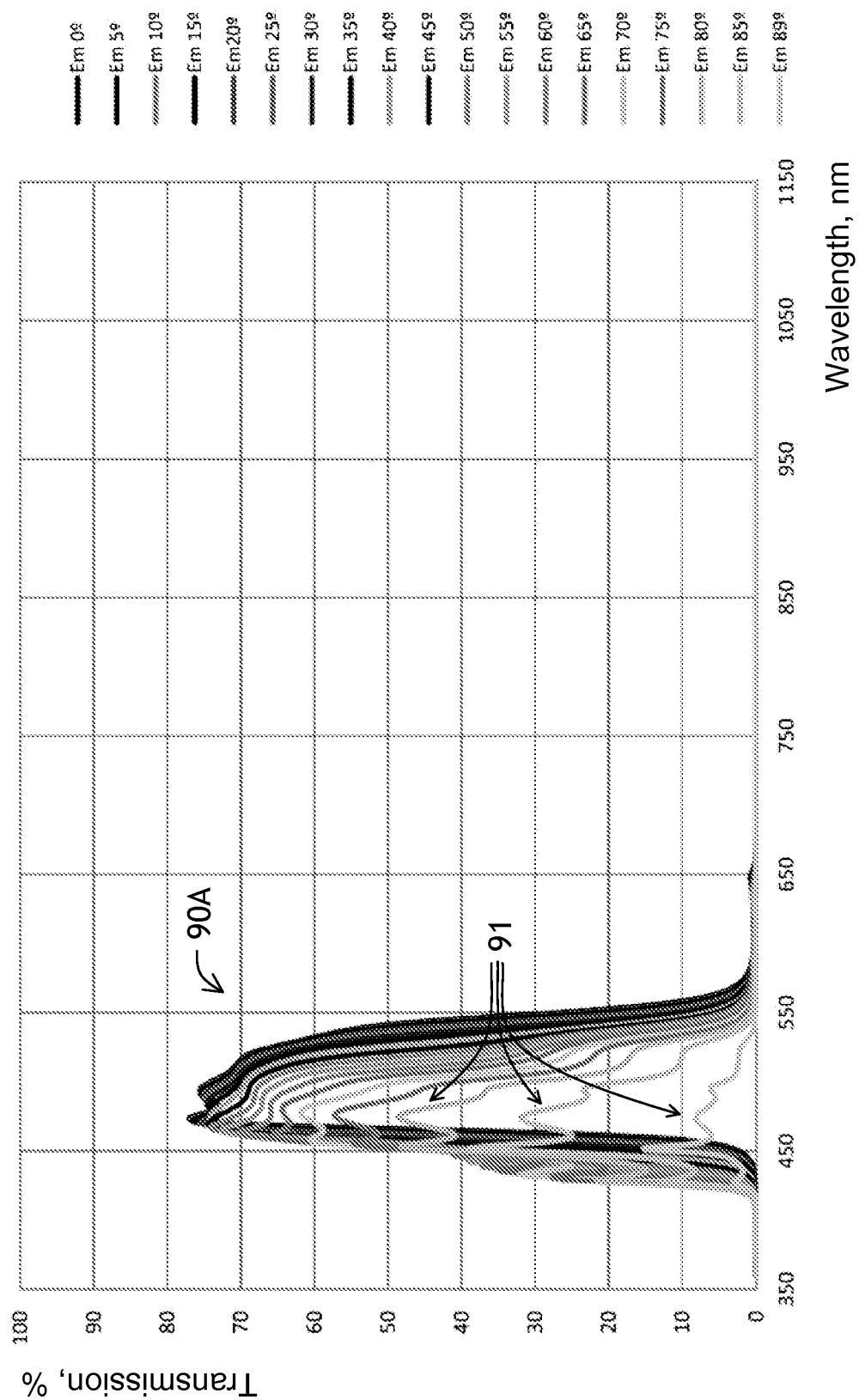
FIG. 9A is a superposition of transmission spectra at different angles of incidence of a metal-dielectric filter of the invention.
Figure 9B:
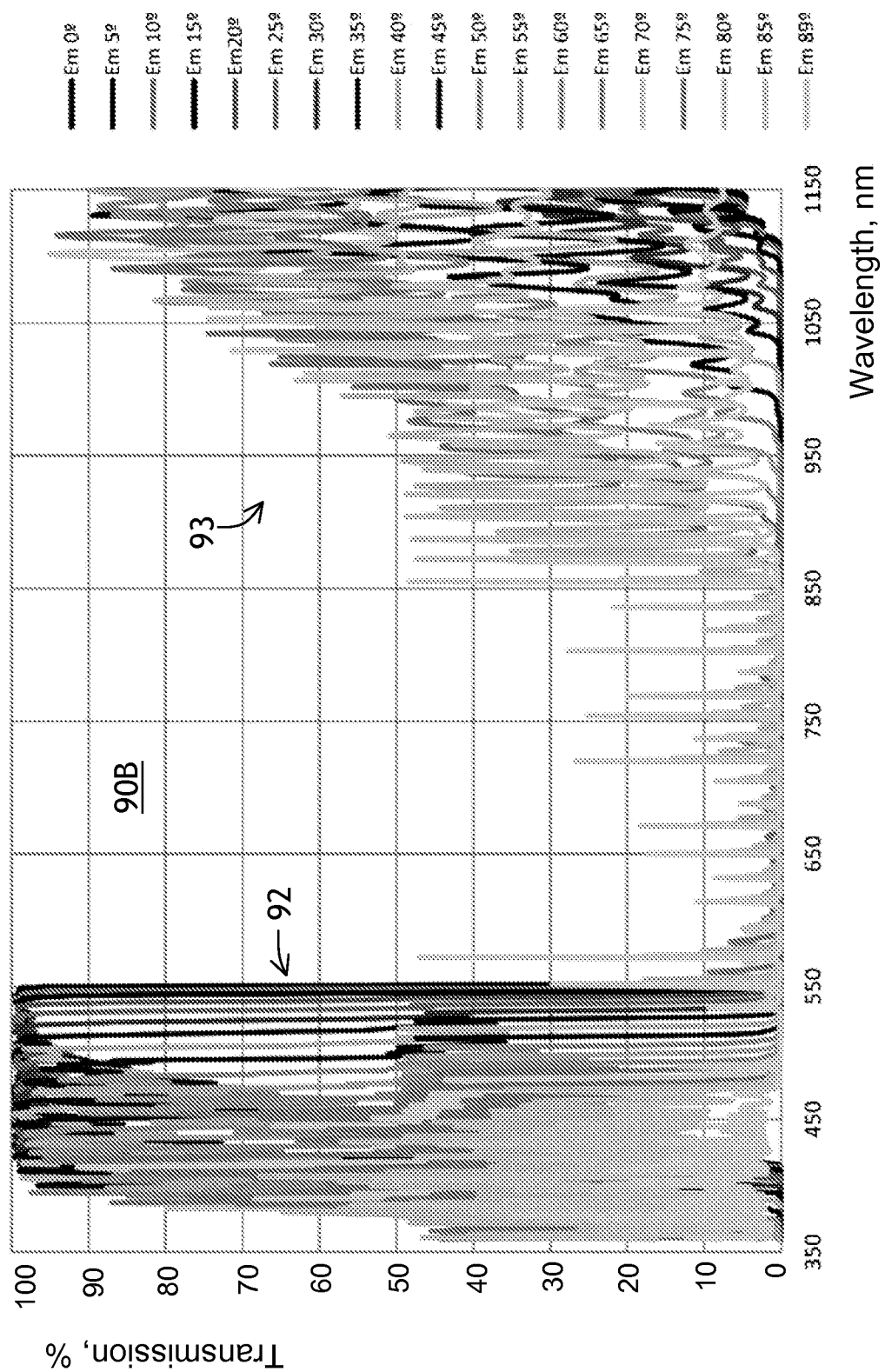
FIG. 9B is a superposition of transmission spectra at different angles of incidence of a typical dielectric stack filter.

As noted above, using metal-dielectric filters 22, 22A, 22B, 42, 42A, 42B allows one to lessen angular sensitivity of the corresponding transmission wavelengths $\lambda_F$, $\lambda_{F1}$, $\lambda_{F2}$, $\lambda_E$, $\lambda_{E1}$, and $\lambda_{E2}$, as compared to commonly used dielectric stack filters, thus facilitating spectrometer size reduction. The angular sensitivity of various filters will now be illustrated. Referring to FIG. 9A, example optical transmission spectra 90A of the excitation optical filter 42 are shown for angles of incidence between 0 degrees (normal incidence) and 89 degrees (oblique incidence), with the step of 5 degrees except for the last step of 4 degrees. The filter includes five 16 nm to 42 nm thick silver layers sandwiched between six 60 nm to 70 nm thick $Ta_2O_5$ layers, and is immersed into a medium having a refractive index of 1.564. One can see that changing the angle of incidence does not shift the center wavelength or position of band edges of the excitation optical filter 42, only reducing the amplitude of transmission, and introducing ripple 91 at high angles of incidence. Turning for comparison to FIG. 9B with further reference to FIG. 9A, optical transmission spectra 90B of a typical dielectric stack optical filter having a similar passband as in FIG. 9A and immersed into a medium with the same index of refraction, are shown for same angles of incidence ranging between 0 degrees (normal incidence) and 89 degrees (oblique incidence), with the step of 5 degrees except for the last step of 4 degrees. One can see at 92 that as the angle of incidence changes, the band edge wavelength shifts, and secondary transmission bands appear at 93.

Figure 9C:
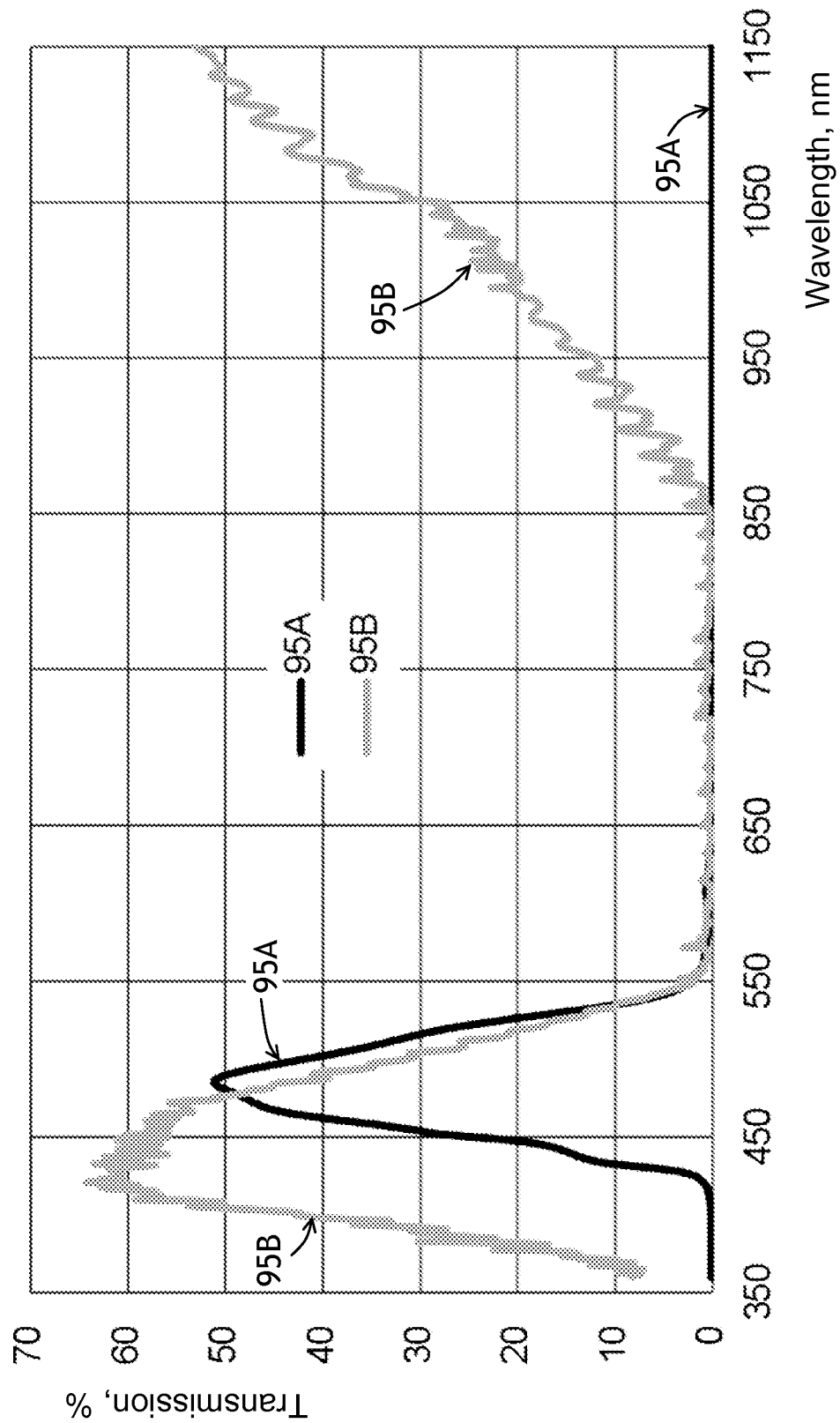
FIG. 9C is a superposition of averaged transmission spectra of FIGS. 9A and 9B.

Referring to FIG. 9C, averaged spectral plots 95A of the spectra 90A of FIG. 9A; and 95B of the dielectric stack filter spectra 90B of FIG. 9B are brought together for comparison. The reduced angular sensitivity of the transmission wavelengths $\lambda_F$, $\lambda_{F1}$, $\lambda_{F2}$, $\lambda_E$, $\lambda_{E1}$, and $\lambda_{E2}$ of the optical filters 22, 22A, 22B, 42, 42A, 42B, respectively, enables the spectrometer assemblies 20, 40A to 40D, and 50 of FIGS. 2A, 4A to 4D, and 5, respectively, to be more compact.

Figure 10A:
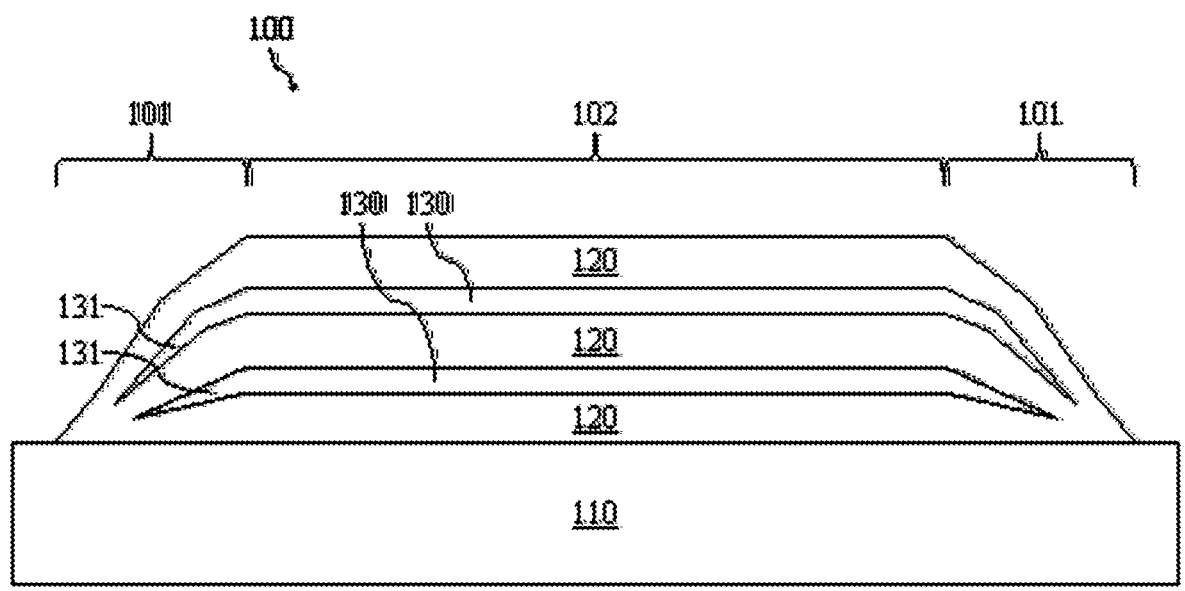
FIG. 10A is a side cross-sectional view of an encapsulated metal-dielectric filter according to an embodiment of the invention.

A manufacturing process of a metal-dielectric filter usable in the invention will now be considered. Turning to FIG. 10A with further reference to FIGS. 2A and 2B, FIGS. 4A to 4D, FIG. 5, and FIG. 7, an optical filter 100 is a variant of the signal filter 22 of FIGS. 2A and 2B and/or the excitation optical filter 42 of FIGS. 4A to 4D, and is usable in the spectrometer assemblies 10, 40A to 40D, 50, and 70 of FIG. 2A, FIGS. 4A to 4D, FIG. 5, and FIG. 7, respectively. The optical filter 100 includes three dielectric layers 120 and two metal layers 130 stacked in alternation. The optical filter 100 is disposed on a substrate 110. The metal layers 130 are each disposed between and adjacent to two dielectric layers 120, which protect the metal layers 130 from corrosion.

The metal layers 130 have tapered edges 131 at a periphery 101 of the optical filter 100. The metal layers 130 are substantially uniform in thickness throughout a central portion 102 of the optical filter 100, but taper off in thickness at the periphery 101 of the optical filter 100. Likewise, the dielectric layers 120 are substantially uniform in thickness throughout the central portion 102 of the optical filter 100, but taper off in thickness at the periphery 101. Accordingly, the central portion 102 of the optical filter 100 is substantially uniform in height, whereas the periphery 101 of the optical filter 100 is sloped. The optical filter 100 has a substantially flat top and sloped sides.

Advantageously, the tapered edges 131 of the metal layers 130 are not exposed to the environment. Rather, the tapered edges 131 of the metal layers 130 are covered by one or more of the dielectric layers 120. The one or more dielectric layers 120 suppress environmental degradation, e.g., corrosion, of the metal layers 130, e.g., by inhibiting the diffusion of sulfur and water into the metal layers 130. Preferably, the metal layers 130 are substantially encapsulated by the dielectric layers 120.

Figure 10B:
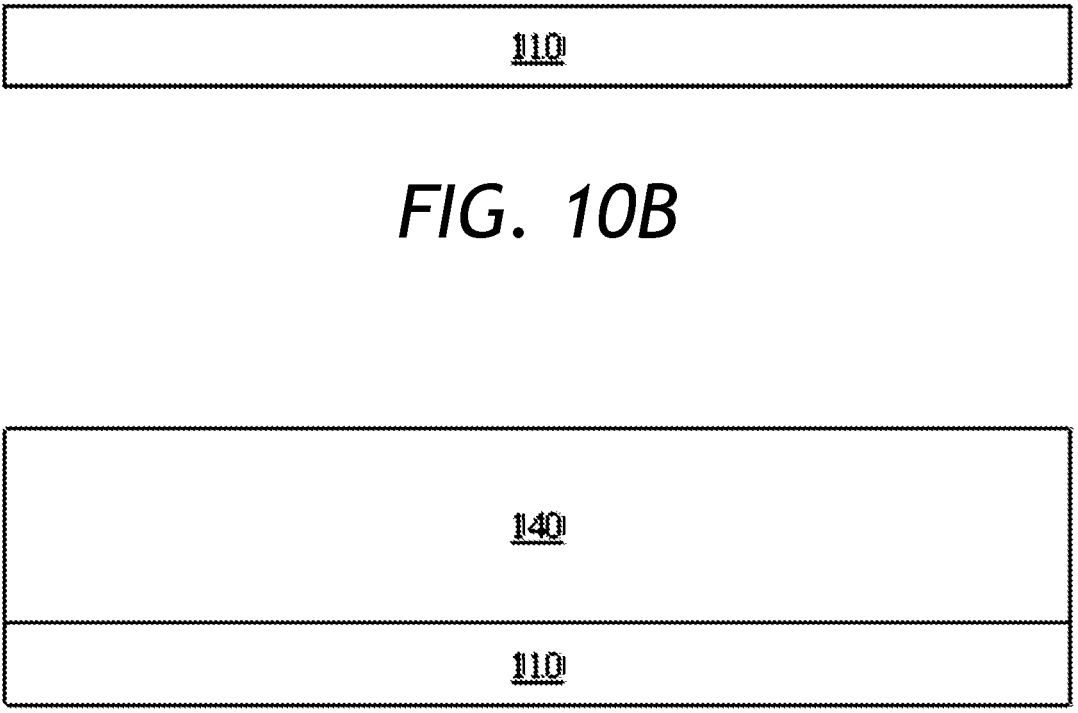
FIGS. 10B to 10G are cross-sectional views of a wafer illustrating manufacturing process of the filter of FIG. 10A.
Figure 10C:
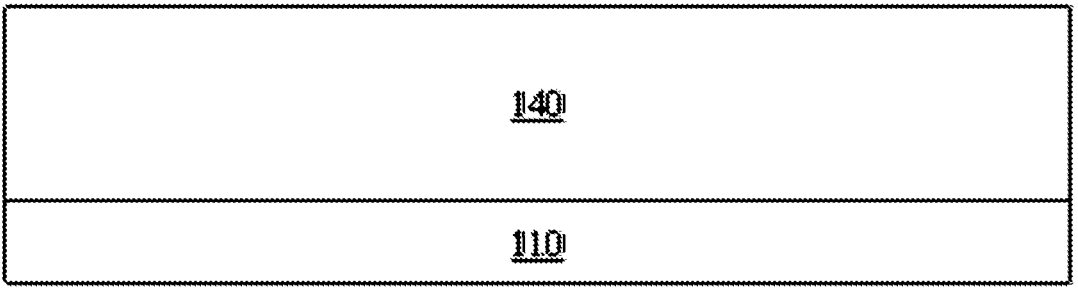

With reference to FIGS. 10B to 10G, the first embodiment of the optical filter 100 may be fabricated by a lift-off process. In a first step, the substrate 110 is provided (FIG. 10B). In a second step, a photoresist layer 140 is applied onto the substrate 110 (FIG. 10C). Typically, the photoresist layer 140 is applied by spin coating or spray coating.

Figure 10D:
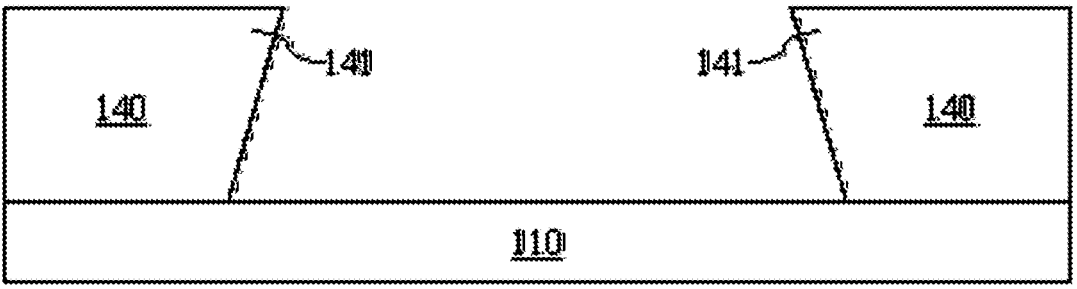

In a third step, the photoresist layer 140 is patterned to uncover a region of the substrate 110 where the optical filter 100 is to be disposed, that is, a filter region (FIG. 10D). Other regions of the substrate 110 remain covered by the patterned photoresist layer 140. Typically, the photoresist layer 140 is patterned by first exposing a region of the photoresist layer 140 covering the filter region of the substrate 110 to ultraviolet (UV) light through a mask, and then developing, for example etching, the exposed region of the photoresist layer 140 by using a suitable developer or solvent. The photoresist layer 140 is preferably patterned in such a manner that an overhang 141 is formed in the patterned photoresist layer 140 surrounding the filter region. In some cases, the photoresist layer 140 consists of two different materials. This makes it easier to create the overhang, or undercut 141.

Figure 10E:
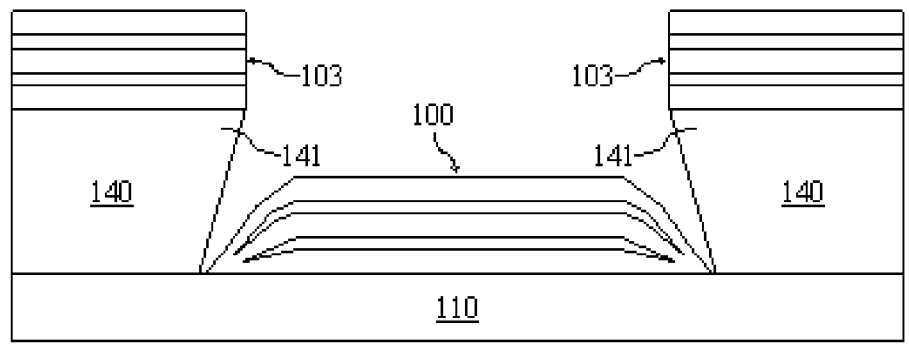

In a fourth step, a multilayer stack 103 is deposited onto the patterned photoresist layer 140 and the filter region of the substrate 110 (FIG. 10E). A portion of the multilayer stack 103 disposed on the filter region of the substrate 110 forms the optical filter 100. The layers of the multilayer stack 103, which correspond to the layers of the optical filter 100, may be deposited by using a variety of deposition techniques, such as: evaporation, e.g., thermal evaporation, electron-beam evaporation, plasma-assisted evaporation, or reactive-ion evaporation; sputtering, e.g., magnetron sputtering, reactive sputtering, alternating-current (AC) sputtering, direct-current (DC) sputtering, pulsed DC sputtering, or ion-beam sputtering; chemical vapor deposition, e.g., plasma-enhanced chemical vapor deposition; and atomic layer deposition. Different layers may be deposited by using different deposition techniques.

Because the overhang 141 shadows a periphery of the filter region of the substrate 110, the deposited layers taper off in thickness towards the periphery 101 of the optical filter 100. When a dielectric layer 120 is deposited onto a metal layer 130, the dielectric layer 120 covers not only the top surface of the metal layer 130, but also the tapered edges 131 of the metal layer 130, thereby protecting the metal layer 130 from the environment.

Figure 10F:
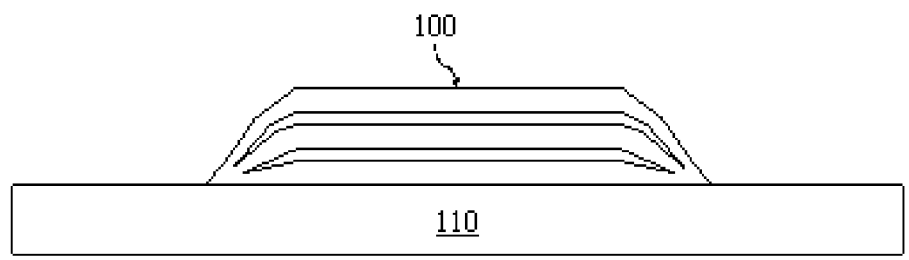
Figure 10G:
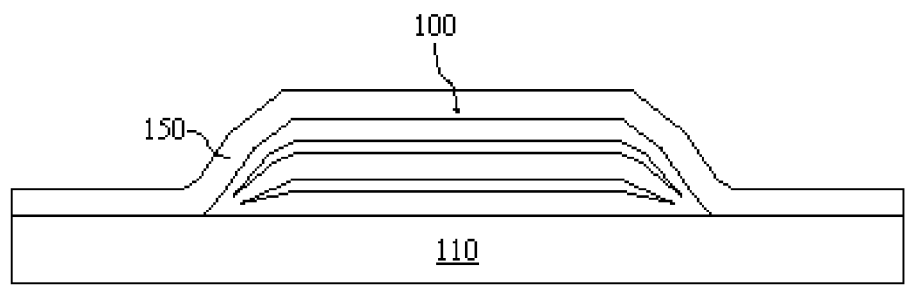

In a fifth step, a portion of the multilayer stack 103 on the patterned photoresist layer 140 is removed, that is, lifted off, together with the photoresist layer 140 (FIG. 10F). Typically, the photoresist layer 140 is stripped by using a suitable stripper or solvent. The optical filter 100 remains on the filter region of the substrate 110. In an optional sixth step, an additional dielectric coating 150 is deposited onto the optical filter 100. The dielectric coating 150 covers both the central portion 102 and the periphery 101 of the optical filter 100, thereby protecting the optical filter 100 from the environment.

Figure 11A:
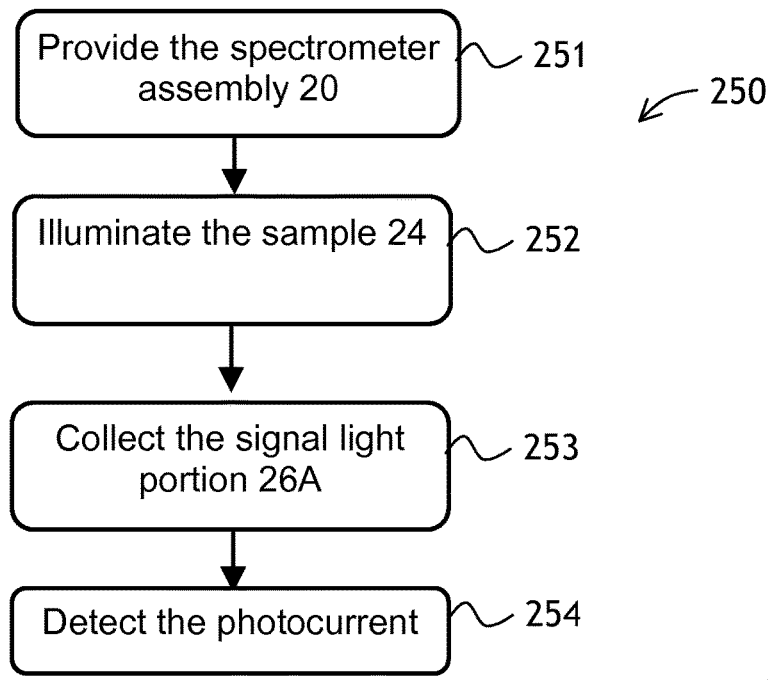
FIGS. 11A and 11B are flow charts of methods of detecting fluorescence according to the invention.

Turning to FIG. 11A with further reference to FIGS. 2B, 3, and FIG. 4B, a method 250 for detecting fluorescence includes a step 251 of providing the spectrometer assembly 20. In a step 252, the sample 24 is illuminated with the excitation light portion 25A; in the step 253, the first portion 26A of the signal light 26 is collected in a total collection angle of e.g. at least 60 degrees, or +−30 degrees away from normal incidence; and in a step 254, the electrical signal (e.g. photocurrent) of the photodetector 23 is detected. The collection angle can be as large as +−75 degrees away from the normal incidence, or 150 degrees total.

Figure 11B:
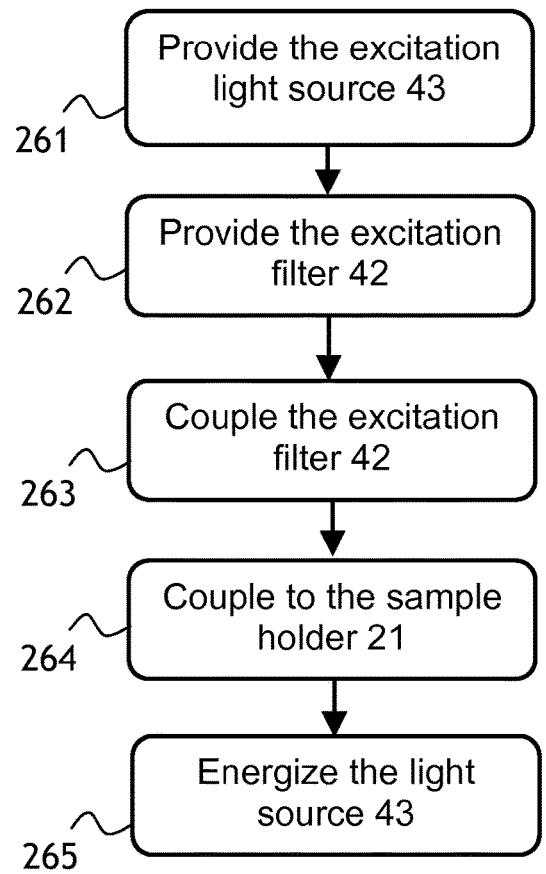

Referring now to FIG. 11B with further reference to FIGS. 2B, 3, and FIG. 4B, the illuminating step 252 can include a step 261 of providing the excitation light source 43. In a step 262, the excitation filter 42 is provided by stacking in alternation continuous, non-micro-structured metal 27 and dielectric 28 layers (FIG. 2B), for transmitting the portion 25A of the excitation light 25 at an excitation wavelength $\lambda_E$ (FIG. 3), while blocking the signal light 26. In a step 263, the excitation filter 42 is coupled to the excitation light source 43. In a step 264, the sample holder 21 is coupled to the excitation filter 42 for receiving the portion 25A of the excitation light 25 transmitted through the excitation filter 42. In a step 264, the sample holder 21 is coupled to the excitation filter 42 for receiving the portion 25A of the excitation light 25 transmitted through the excitation filter 42. Finally, in a step 265, the excitation light source 43 is energized.

The foregoing description of one or more embodiments of the invention has been presented for the purposes of illustration and description. It is not intended to be exhaustive or to limit the invention to the precise form disclosed. Many modifications and variations are possible in light of the above teaching. For example, spectrometer assemblies disclosed herein can be used not only for detecting fluorescence, but for detecting multiphoton fluorescence, nonlinear scattering such as optical harmonic scattering of the excitation light, surface-enhanced nonlinear optical scattering and fluorescence, and the like, with the corresponding adjustment of the transmission wavelengths of the optical filters used. Light sources used can include laser diodes, light-emitting diodes (LED) including white LEDs, and the like.

What is claimed is:

1. A sensor comprising:
   a photodetector configured to convert received light into a current indicative of an intensity of the received light; and
   an optical filter configured to:
      prevent light having a wavelength outside a bandpass region from reaching the photodetector, and
      pass light having a wavelength within the bandpass region to the photodetector,
         wherein a percentage of light passing through the optical filter decreases as an angle of incidence of light increases from 0 degrees to 89 degrees, and
         wherein an amplitude of transmission decreases as the angle of incidence of light increases.

2. The sensor of claim 1, wherein the optical filter is a low angle sensitive optical filter.

3. The sensor of claim 1, wherein the optical filter has low sensitivity to high angle incident light.

4. The sensor of claim 1, wherein the optical filter is less sensitive to the angle incidence of light than a micro-structured metal-dielectric filter.

5. The sensor of claim 1, wherein the optical filter is a nanostructured filter.

6. The sensor of claim 1, wherein the optical filter comprises layers of metal and oxides.

7. The sensor of claim 6, wherein the layers of metal and oxides have a thickness configured to pass light within the bandpass region.

8. The sensor of claim 6, wherein the layers of metal and oxides are deposited on the photodetector.

9. The sensor of claim 8, wherein the layers of metal and oxides are deposited on the photodetector by magnetron sputter coating.

10. The sensor of claim 6,
wherein the photodetector includes an exit side opposite a receiving side, and
wherein the layers of metal and oxides are deposited on the exit side of the photodetector.

11. The sensor of claim 1, wherein the bandpass region shifts by 20 nm or less as the angle of incidence of light received by the optical filter increases from 0 degrees to 89 degrees.

12. The sensor of claim 1, further comprising:
an element configured to emit emission light toward the optical filter; and
a light source configured to irradiate excitation light to the element.

13. The sensor of claim 12, wherein the element is positioned relative to a receiving surface of the optical filter such that at least a portion of the emission light reaches the optical filter as low angle of incidence light.

14. The sensor of claim 13, wherein the low angle of incidence light has an angle of incidence less than or equal to 25 degrees.

15. The sensor of claim 13, wherein the low angle of incidence light has an angle of incidence less than or equal to 20 degrees.

16. The sensor of claim 13, wherein the low angle of incidence light has an angle of incidence less than or equal to 15 degrees.

17. The sensor of claim 13, wherein the low angle of incidence light has an angle of incidence less than or equal to 10 degrees.

18. The sensor of claim 13, wherein the low angle of incidence light has an angle of incidence less than or equal to 5 degrees.

19. The sensor of claim 1, wherein the optical filter utilizes dichroic and absorptive filtering.

20. The sensor of claim 1,
wherein the photodetector is a first photodetector,
wherein the optical filter is a first optical filter,
wherein the bandpass region is a first bandpass region, and
wherein the sensor further comprises:
a second photodetector configured to:
convert different received light into a different current indicative of a different intensity of the different received light received by the second photodetector; and
a second optical filter configured to:
prevent different light having a wavelength outside a second bandpass region from reaching the second photodetector, and
pass different light having a wavelength within the second bandpass region to the second photodetector.

21. A method of detecting an analyte using a sensor, the method comprising:
irradiating, by a light source of the sensor, excitation light to an analyte indicator of the sensor;
emitting, by the analyte indicator, emission light to an optical filter of the sensor;
receiving, by the optical filter, light that includes the emission light emitted by the analyte indicator;
preventing, by the optical filter, first light, of the received light, having one or more of a wavelength outside a bandpass region or a high angle of incidence from reaching a photodetector of the sensor;
passing, by the optical filter, second light, of the received light, having a wavelength within the bandpass region to the photodetector,
wherein a percentage of light passed by the optical filter decreases as an angle of incidence of light increases from 0 degrees to 89 degrees, and
wherein an amplitude of transmission decreases as the angle of incidence of light increases; and
receiving, by the photodetector, the passed light.

22. A method of manufacturing an analyte sensor, the method comprising:
fabricating or mounting a photodetector in or on a substrate; and
forming an optical filter by depositing layers of metal and oxides on the photodetector,
wherein the optical filter is configured to prevent light having a wavelength outside a bandpass region from reaching the photodetector and to pass light having a wavelength within the bandpass region to the photodetector,
wherein a percentage of light passed through the optical filter decreases as an angle of incidence of light increases from 0 degrees to 89 degrees, and
wherein an amplitude of transmission decreases as the angle of incidence of light increases.

* * * * *